United States Patent [19]

Bueche et al.

[11] Patent Number: 5,851,172
[45] Date of Patent: Dec. 22, 1998

[54] AFTERLOADER WITH ACTIVE FORCE FEEDBACK

[75] Inventors: Kenneth M. Bueche, Friendswood; Richard T. Thornton, League City; Anthony J. Bradshaw, Missouri City, all of Tex.

[73] Assignee: Omnitron International, Inc., Houston, Tex.

[21] Appl. No.: 436,075

[22] Filed: May 8, 1995

[51] Int. Cl.[6] .................................................. A61N 5/00
[52] U.S. Cl. .................................................. 600/7; 600/3
[58] Field of Search ............................................ 600/1–8

[56] References Cited

U.S. PATENT DOCUMENTS

| | | | |
|---|---|---|---|
| 4,851,694 | 7/1989 | Rague et al. | 600/3 |
| 5,030,194 | 7/1991 | Van't Hooft | 600/7 |
| 5,084,001 | 1/1992 | Van't Hooft et al. | 600/3 |
| 5,092,834 | 3/1992 | Bradshaw et al. | 600/7 |

FOREIGN PATENT DOCUMENTS

| | | | |
|---|---|---|---|
| 3335438 | 4/1985 | Germany | 600/12 |
| 3643893 | 6/1988 | Germany | 600/7 |
| 0649412 | 3/1979 | U.S.S.R. | 600/3 |

*Primary Examiner*—John P. Lacyk
*Attorney, Agent, or Firm*—Wigman, Cohen, Leitner & Myers, P.C.

[57] ABSTRACT

An afterloader for use in radiation oncology or intravascular radiotherapy comprises a wire storage mechanism for storing a radioactive-tipped sourcewire, a drive mechanism for advancing the sourcewire into a catheter or other channel implanted in a patient. A computer control system receives information from an encoder and a force sensor, which monitor the displacement of and the force exerted on the sourcewire, respectively. The displacement and force information are used to advance the wire at the fastest possible speed to the treatment site without exceeding a pre-programmed force profile designed to ensure the sourcewire does not puncture the catheter. The force profile is dynamic depending on the particular catheter being used, and catheter information may be inputted into the computer controller using a bar code or other information storage means in the catheter itself.

41 Claims, 7 Drawing Sheets

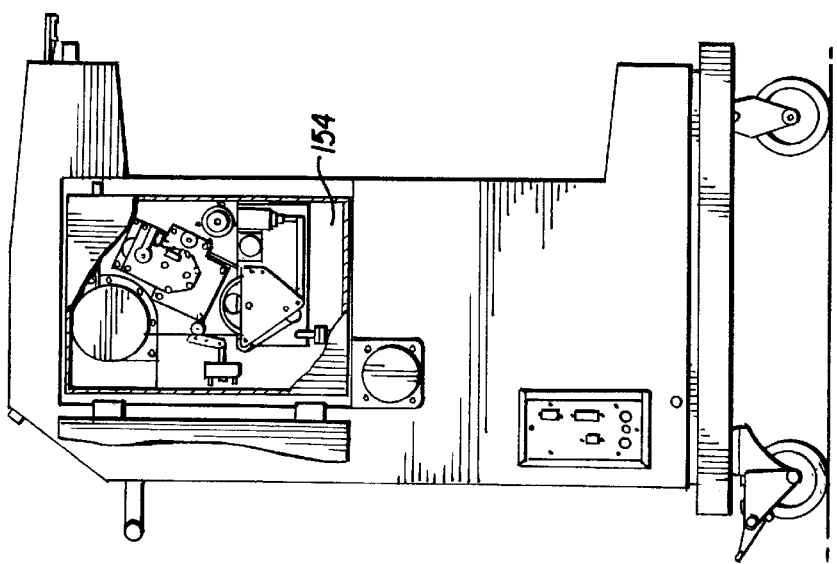
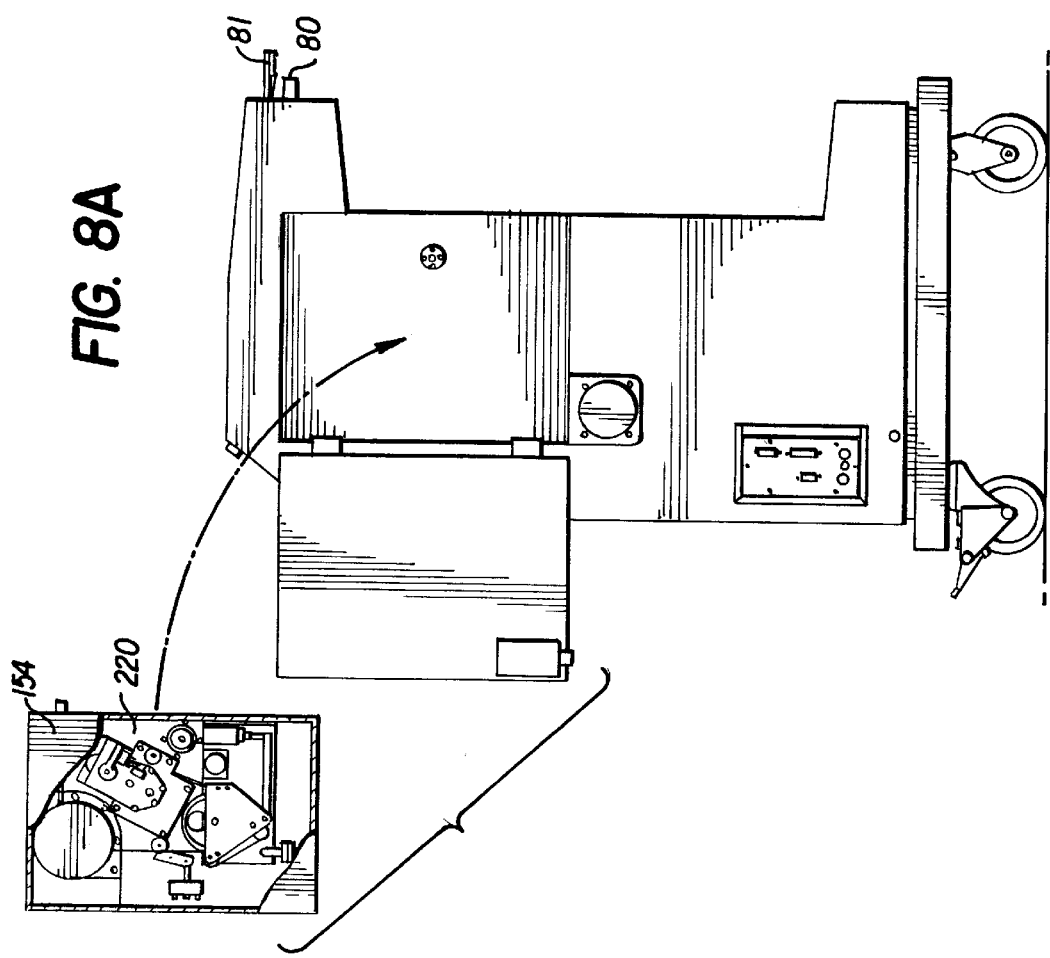

AFTERLOADER WITH ACTIVE FORCE FEEDBACK

BACKGROUND OF THE INVENTION

This invention relates to methods and apparatus for the handling and precise positioning of radioactive sources used in radiation oncology and intravascular radiotherapy, particularly to a device known as an afterloader, which advances a wire or cable having a radioactive source at the tip along a catheter or other closed pathway to a position within the body of a patient for a predetermined period of time and which thereafter withdraws the wire and radioactive source from the patient.

It is known in the medical field to use afterloader devices in the treatment of cancerous tumors using radioactive sources having intensity greater than that which can safely be handled. Typically one or more catheters, needles, or other closed pathways (hereafter "catheters") to the treatment site are positioned in the patient. The catheters are then attached to the afterloader which advances the radioactive source at the end of the wire, sometimes called a sourcewire, along the catheters according to a predetermined sequence calculated to deliver a therapeutic dose of radiation to the tumor.

Less well known but rapidly gaining acceptance is the use of radiation to prevent or inhibit restenosis following percutaneous transluminal coronary angioplasty (PTCA) or other arterial lumen opening procedure. PTCA, also known as balloon angioplasty, is the predominant treatment for coronary vessel stenosis. Approximately 300,000 procedures were performed in the United States (U.S.) in 1990 and an estimated 400,000 in 1992. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% of all patients requiring repeat PTCA procedures or by-pass surgery, with attendant high cost and added patient risk. More recent attempts to prevent restenosis by use of drugs, mechanical devices, and other experimental procedures have had limited success.

Restenosis occurs as a result of injury to the arterial wall during the lumen opening angioplasty procedure. In some patients, the injury initiates a repair response that is characterized by hyperplastic growth of the vascular smooth muscle cells in the region traumatized by the angioplasty. The hyperplasia of smooth muscle cells narrows the lumen that was opened by the angioplasty, thereby necessitating a repeat PTCA or other procedure to alleviate the restenosis.

Preliminary studies indicate that intravascular radiotherapy (IRT) has promise in the prevention or long-term control of restenosis following angioplasty. It is also believed that IRT may be used to prevent stenosis following cardiovascular graft procedures or other trauma to the vessel wall. A proposed IRT method disclosed in co-pending application Ser. No. 08/057,322 is first to advance a flexible catheter (radioguide catheter) through the cardiovascular system of the patient until the distal tip is at or near the region of the vessel that has been subjected to the angioplasty procedure. Subsequently, a sourcewire is advanced, preferably by an afterloader, along the radioguide catheter until the radiation source is disposed at the affected region. The radiation source is held at the affected region for a predetermined treatment period calculated to deliver an effective dose of radiation, then is withdrawn.

It will be appreciated from the foregoing that highly accurate positioning of the source within the patient is essential to maximize the effectiveness of the treatment while minimizing the damage to adjacent healthy tissue. It will also be appreciated that the source must be advanced to the treatment site as quickly as possible to minimize injury to healthy tissue along the catheter leading from outside the body of the patient to the treatment site.

To minimize trauma to sensitive tissue, the catheters and sourcewires that are used in sensitive areas are chosen to be as small as practicable, typically on the order of 0.5 millimeters. Use of these small diameter sourcewires presents special problems for the afterloader, for the small diameter wire does not have sufficient column strength to be driven into the catheter unless the afterloader design incorporates special precautions to prevent buckling. These problems associated with the potential buckling of the sourcewire are compounded by the need for rapid advancement of the sourcewire to avoid damaging healthy tissue.

Another problem is presented that is unique to the IRT application. In order to reach the site where the PTCA has been performed, the IRT sourcewire must often follow a tortuous pathway through the narrow twisted openings of the coronary arteries. In order to avoid blocking blood flow in these narrow openings, use of the smallest possible radioguide catheter and sourcewire is often required. If, however, the tiny radioguide catheter becomes kinked or otherwise obstructed as it is implanted, unless the obstruction is detected, the afterloader may drive the sourcewire through the wall of the catheter and even through the wall of the patient's blood vessel, with dire consequences.

Accordingly, it is a principal object of the present invention to provide an afterloader having an active force feedback to enable the afterloader to drive a sourcewire through a catheter or other pathway at the highest possible speed without risk of puncturing a catheter or buckling the sourcewire.

Another significant object of the present invention is to provide separate sourcewire storage means and drive means thereby facilitating the maintenance of a minimal fixed distance between the drive means and the guide tube leading to the catheter, thereby minimizing the chance of buckling the sourcewire.

Yet another significant object of the present invention is to automatically provide information to the control system of the afterloader concerning the identity of the catheter being used, thereby facilitating automatic adjustments of speed and force responsive to the particular catheter.

SUMMARY OF THE INVENTION

According to the present invention, an afterloader is provided having a sensor to monitor the force being imparted to the sourcewire as it is being driven out of the afterloader into the catheter toward the treatment site. The output of the force sensor is fed back to the control system, comprising the circuitry and software that operates the afterloader drive mechanism. Responsive in part to the signal from the force sensor, the control system may increase or decrease the speed of advancement of the sourcewire or may cause the sourcewire to be withdrawn. By providing a force feedback to a controller, as opposed merely to limiting the maximum force imparted to the source wire, the maximum safe speed and force is applied to the sourcewire dynamically, thereby minimizing incidental tissue damage and maximizing safety.

Recognizing that different catheters may have different coefficients of friction or may have other attributes that affect the maximum force that can safely be imparted to an advancing sourcewire, an embodiment of the present invention includes a scanner adapted to read information from the catheter. Information from the catheter is used by the control system to adjust the maximum safe speed and/or force imparted to the advancing sourcewire.

In an embodiment of the present invention the wire storage means is separate from the drive system to facilitate close placement of a wire guide adjacent to the drive system to reduce chances of buckling the sourcewire and to minimize wire degradation resulting from frictional wear.

In yet another embodiment of the present invention, particularly suited to low penetration sources, such as substantially pure beta particle emitters, the drive mechanism and wire storage means are incorporated into a readily removable cassette. Use of a cassette enables the sourcewire to be exchanged by relatively unskilled workers as opposed to highly trained technicians.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which:

FIGS. 8A and 8B is a side view illustrating a removable cassette sourcewire storage and drive system.

DESCRIPTION OF PREFERRED
EMBODIMENTS AND METHODS

Figure 1:
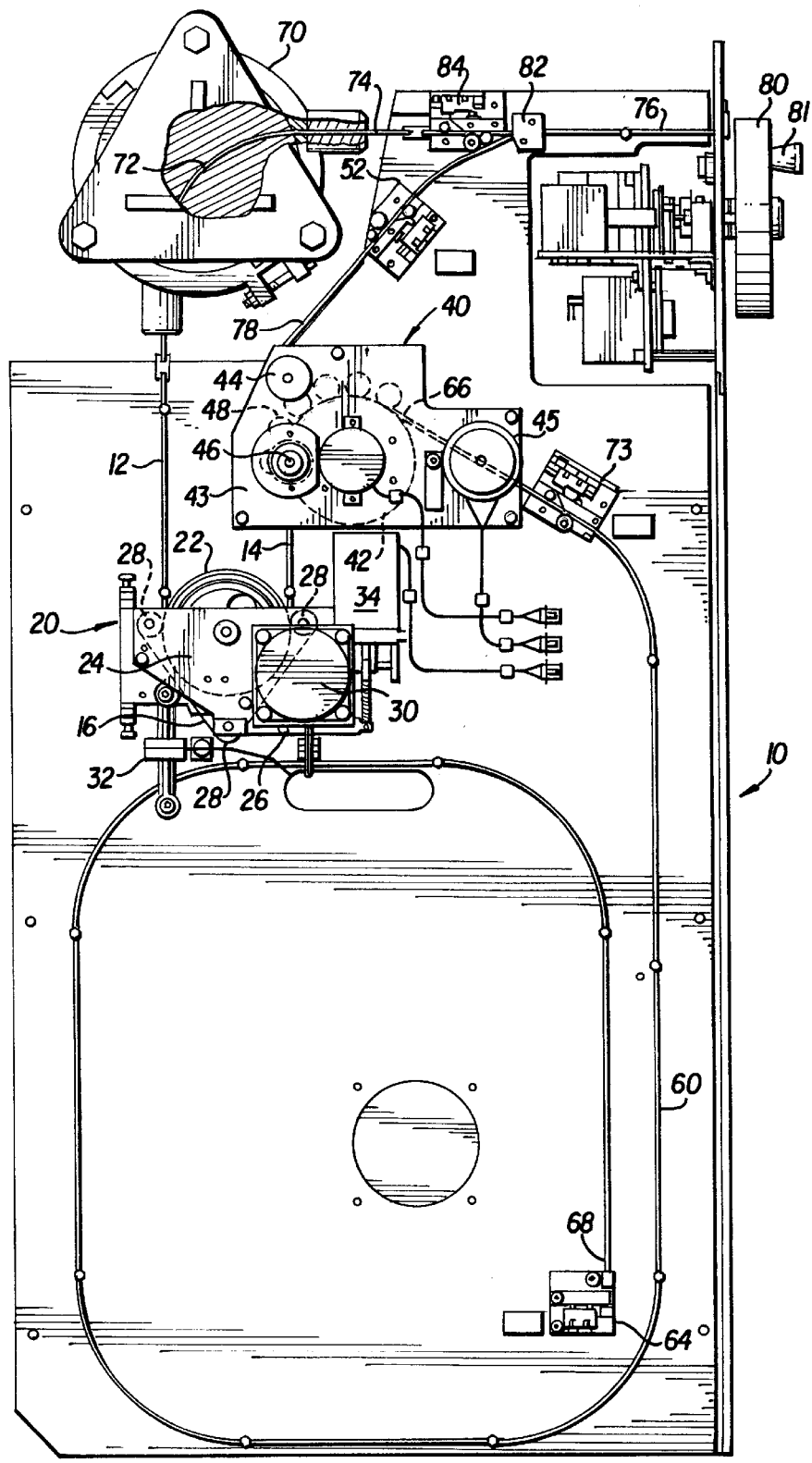
FIG. 1 is a left side view of an embodiment of the present invention with a portion broken away to reveal the sourcewire storage and drive systems.

FIG. 1 is a side view of the left side of an afterloader embodying features of the present invention with portions broken away to reveal features of the sourcewire drive system. The invention comprises an improvement over the afterloader of U.S. Pat. No. 5,092,834 to A. Bradshaw, et al. the specification of which is incorporated herein by this reference (the '834 patent). As disclosed in the aforementioned patent, in a typical treatment scenario, a catheter or other guide is implanted in the patient and guided to the site to be treated. A dummy sourcewire having a radio-opaque tip or other similar non-radioactive wire is then advanced to the maximum treatment distance and retracted to verify that the channel in the catheter is unobstructed. Under fluoroscopy or other imaging process, the dummy wire is advanced in a sequence designed to simulate the treatment sequence as position data is recorded by the computer controller of the afterloader. After the treatment plan is verified by the fluoroscopic images, the treatment is executed automatically by the afterloader using the radioactive-tipped sourcewire.

The afterloader comprises housing 10 which contains drive mechanism 20, storage feed mechanism 40 and storage tube 60. Mounted external to housing 10 and adjacent thereto is radiation safe 70. A sourcewire 62, not shown in FIG. 1 having proximal and distal ends is stored with the radioactive tipped distal end within the confines of radiation safe 70. In the stored configuration, the remainder of sourcewire 62 passes through guide tube 12, around the drive wheel 22 of drive mechanism 20, through transfer tube 14, around encoder wheel 42 of storage feed mechanism 40 and into the open distal end 66 (shown in phantom lines) of storage tube 60. The proximal portion of sourcewire 62 is contained in storage tube 60 with the proximal tip of sourcewire 62 extending out of proximal end 68 of storage tube 60. When in the stored position, the proximal tip of sourcewire 62 is in contact with or otherwise in a position to trigger active park switch 64.

Drive wheel 22 of drive system 20 comprises a thin cylindrical disk having a single groove in the outer circumferential surface thereof adapted to receive the sourcewire 62. The drive wheel 22 is mounted in low friction bearings to a carriage 24 and driven via conventional means such as a flat cogged belt by drive motor 30, which comprises a conventional stepper or servo motor. Endless belt 16 is disposed about capstans 28 and drive wheel 22 and tensioned by tensioner solenoid 34, which comprises a conventional spring loaded solenoid, which biases a capstan 28 away from drive wheel 22. Endless belt 16 holds sourcewire 62 firmly in the groove in drive wheel 22. Carriage 24 is pivotally mounted to housing 10 by pivot 26, preferably with the axis of pivot 26 along the axis of sourcewire 62 at its point of departure from drive wheel 22 into transfer tube 14. Attached to carriage 24 is force sensor 32, which may be a conventional piezoelectric or strain gauge load cell. As sourcewire 62 is advanced into guide tube 12, the force being imparted to sourcewire 62 generates a moment about pivot 26 of carriage 24 which is measured by force sensor 32. By aligning the pivot 26 with the transfer tube, the effects of the force required to retrieve the sourcewire from the storage tube 60 are eliminated. Preferably, the total mass of carriage 24 is also kept to a minimum to minimize the inertial effects of the carriage mass on the measurement of sourcewire force.

In an alternate embodiment, drive motor 30 is a servo motor and force sensor 32 comprises a conventional current measuring circuit that monitors the current required by drive motor 30 to advance sourcewire 62. Since the current required by a servo motor is proportional to the torque produced by the motor, measurement of current gives an indication of the torque (force) being imparted to the sourcewire. However, this method may introduce some measurement error because unless otherwise compensated, the torque measurement would include the effects of the torque required to retrieve the sourcewire from the storage tube 60.

Figure 2:
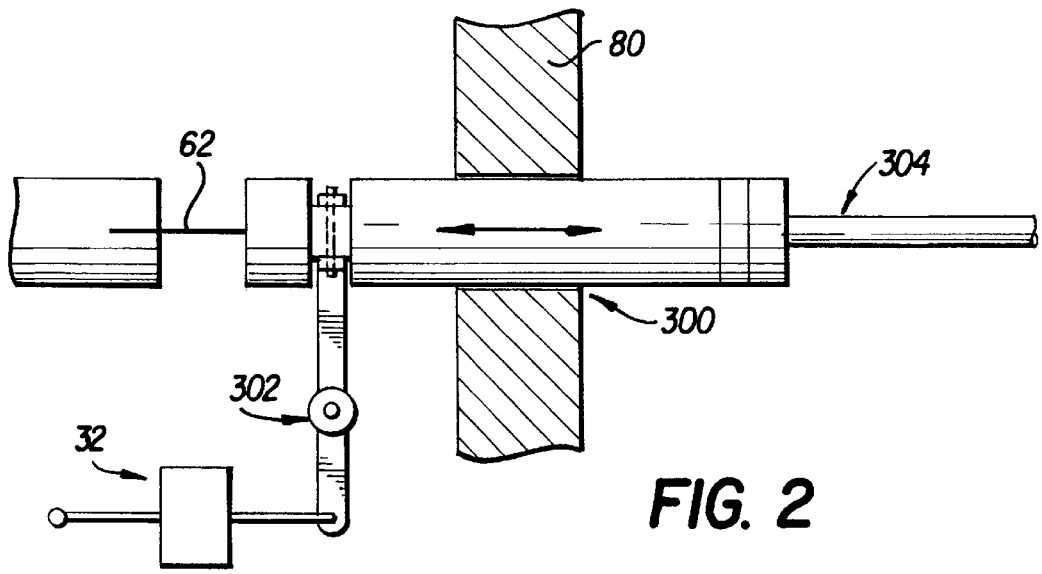
FIG. 2 is a plan view of a slidable catheter force sensor according to the present invention.
Figure 3:
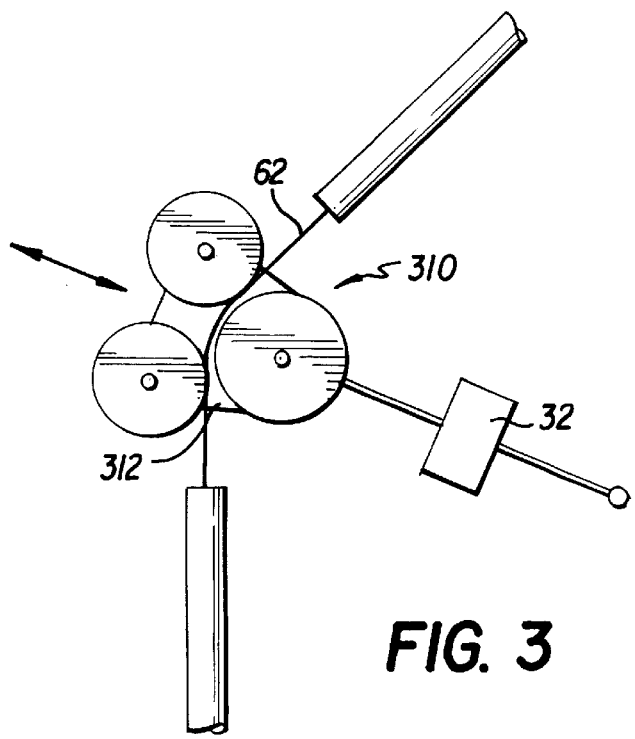
FIG. 3 is a plan view of a direction changing capstan force sensor according to the present invention.

It should be understood that any method that measures force in the wire, as opposed to merely limiting that force, is within the scope of this invention. Accordingly, as shown in FIG. 2, the force sensing mechanism may comprise a catheter adapter 300 slidably mounted in turret 80 and attached to the proximal end of a treatment catheter 304. The force imparted to the wire will tend to move catheter adapter 300 out of turret 80. A force sensor 32 adapted to resist movement of catheter adapter, such as a conventional strain gauge fixed to an end of a pivotally mounted retainer 302, measures the reactive force for input to the control system. Similarly, as shown in FIG. 3, force sensing may be accomplished by passing the wire over a direction changing capstan 310 in such a way that the wire changes direction. Roller 310 is pivotally mounted on a subframe 312 which is slidably or pivotally mounted to housing 10 with the linear or pivotal motion resisted by force sensor 32. The force exerted on the wire is reacted against subframe 312 and sensed by force sensor 32.

It should be noted that by providing a drive wheel 22 that is separate from the wire storage means, the sourcewire has a fixed point of departure from the drive wheel, thereby facilitating close proximity between guide tube 12 and the point of departure of sourcewire 62 from drive wheel 22. Minimizing the amount of sourcewire that is exposed between the drive wheel and the guide tube minimizes the chances of sourcewire 62 buckling as it is driven into guide tube 12.

Opposite drive wheel 22 from guide tube 12 is transfer tube 14 which guides sourcewire 62 from the drive wheel 22 to the encoder wheel 42 of storage feed mechanism 40. Opposite encoder wheel 42 from transfer tube 14 is distal end 66 of storage tube 60. Storage tube 60 comprises a single continuous or a plurality of individual stainless steel tubes or other low friction channels which are attached to housing 10 as described in the foregoing '834 patent. Encoder wheel 42 comprises a thin cylindrical disk having a single groove in the outer circumferential surface thereof adapted to receive the sourcewire 62. The encoder wheel 42 is mounted in low friction bearings to a subhousing 43. Capstans 48 are disposed about the outer circumferential surface of encoder wheel 42 to urge sourcewire 62 against the surface of encoder wheel for a positive rolling engagement therewith. Alternately, a second endless belt similar to belt 16 may be incorporated in lieu of capstans alone to urge sourcewire 62 against encoder wheel 42.

Encoder wheel 42 drives a conventional shaft encoder to measure displacement of the sourcewire 62. It should be noted that by using the word encoder, it is not intended to limit the invention to conventional shaft encoders, but any displacement measuring apparatus. Encoder wheel 42 also serves as the drive wheel for an emergency retract motor which operates in the event of a failure of the main drive mechanism and also serves as the drive wheel for a manual retraction system which can be engaged to retract a sourcewire in the event of a total failure of all power and backup power systems or similar catastrophic failure. In the event of a failure of the main drive, emergency retract motor 44, which comprises a conventional stepper or servo motor, engages encoder wheel by conventional means, such as by engaging a clutch mechanism normally held disengaged by retract solenoid 45, to drive sourcewire 62 into storage tube 60. In the event of a total system failure, manual retract sprocket 46 can be engaged and turned by hand to retract the source wire from the patient. Manual retract sprocket may be equipped with a conventional one-way clutch or similar mechanism to prevent the manual retract mechanism from being operated to advance, rather than retract, the sourcewire 62.

Proximal to the distal end 66 of storage tube 60 is active overtravel switch 73, which comprises an optical or mechanical switch adapted for detecting the presence or absence of sourcewire 62 at a location proximal to distal end 66. In the embodiment of FIG. 1, the switch comprises a conventional mechanical switch with a low friction bearing at the tip, which rides along the surface of sourcewire 62 as it moves into and out of storage tube 60. In the event that the controller were to fail, or the sourcewire were to break inside the storage tube, or if some other failure were to occur that could allow the sourcewire to advance beyond the end of the encoder, the overtravel switch 73 would detect an end of the sourcewire 62 and stop the main drive mechanism 20 from advancing the sourcewire further.

Radiation safe 70 comprises a suitable radiation shielded compartment such as a lead sphere or tungsten cylinder of appropriate size having a tubular guide channel 72 that follows an arcuate path of substantially 90 degrees therethrough. Guide tube 12 is attached to the lower opening of the guide channel 72. The upper opening of guide channel 72 is attached to an upper tubular extension 74 of "Y" connector 82. "Y" connector 82 is, in turn attached to an output guide 76. Preferably "Y" connector 82 is configured so that upper tubular extension 74 is held along a common axis with output guide 76 so that the sourcewire 62 does not have to negotiate an additional bend as it traverses "Y" connector 82. Mounted at the end of output guide 76 of "Y" connector 82 is a turret assembly 80, the general operation of which is described in the aforementioned '834 patent.

Preferably, a scanner 81 is incorporated into turret assembly 80. Catheters approved for use with the afterloader apparatus would contain machine readable information including the type of catheter, the catheter length, balloon length and location, and inventory control number which, as each catheter is inserted into the turret assembly, would be automatically scanned and inputted into the control system 100, which comprises electronic hardware and software for controlling the functions of the afterloader (representatively shown in FIG. 4). Preferably, the information would be fixed in the form of a bar code or similar external coding which would be read by a conventional optical bar code reader. Alternately, a semiconductor chip with the same information embedded in the catheter would be read by a compatible scanner. The scanner 81 may also be separate from turret assembly 80, such as a conventional hand-held bar code reader, or a fixed bar code reader adjacent to the turret assembly 80. In this alternate embodiment, the catheter information would be read typically prior to insertion of the catheter into turret assembly 80.

Mounted along upper tubular extension 76 of "Y" connector 82 is active home sensor 84, which comprises an optical or mechanical switch adapted for detecting the presence or absence of sourcewire 62 in upper tubular extension 74. In the embodiment of FIG. 1, the active home sensor 84 comprises a switch of generally similar construction and operation as overtravel switch 73. The function of active home sensor 84 is to detect the distal end of sourcewire 62 as it is advanced out of safe 70 toward turret 80. The information from home sensor is inputted into control system 100 to provide an accurate indication of the position of the source of sourcewire 62 as it is fed into the catheter attached to turret 80.

Figure 4:
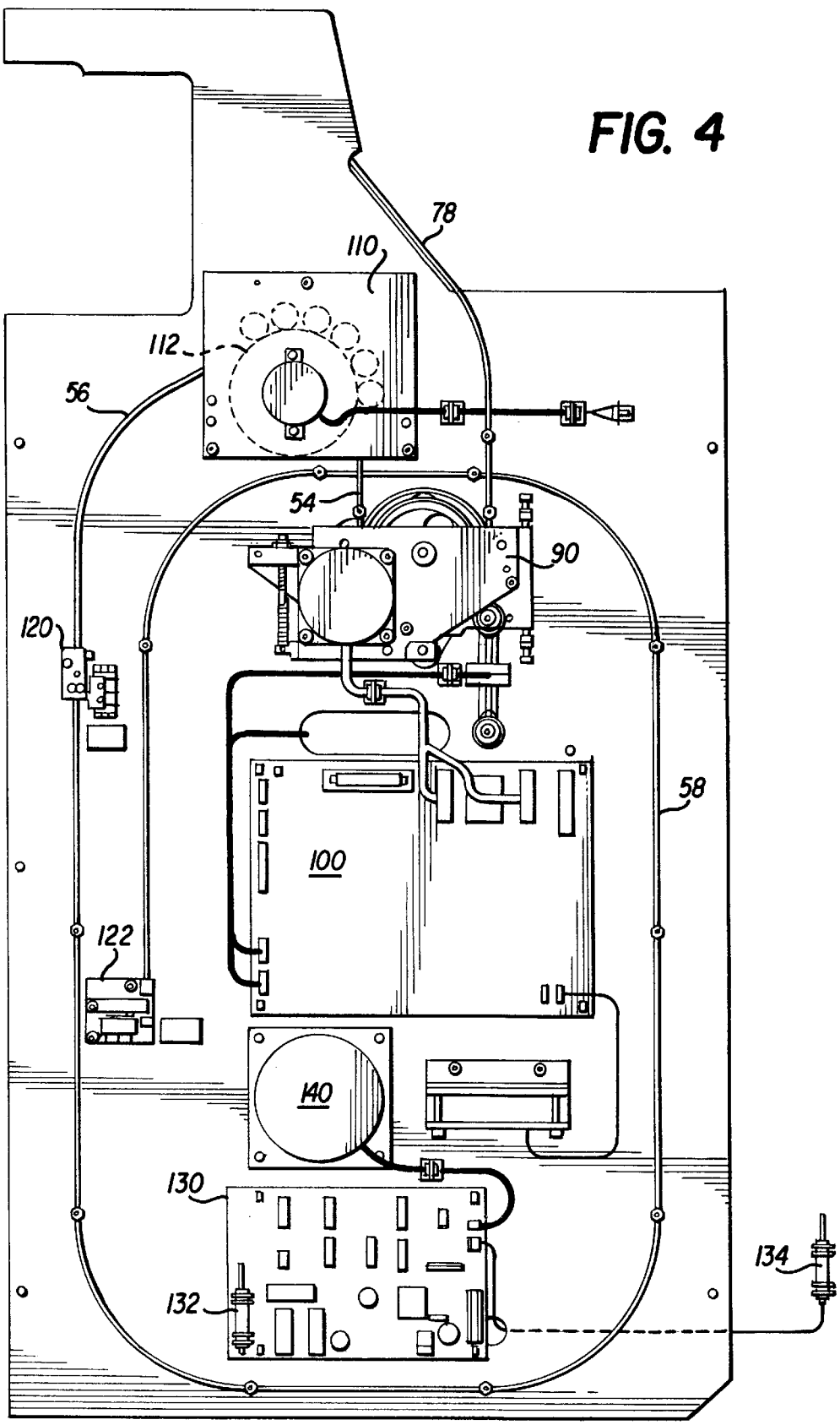
FIG. 4 is a right side view of the embodiment of FIG. 1 with a portion broken away to reveal the dummy wire storage and drive systems.

Attached to the lower opening of "Y" connector 82 is dummy wire guide 78, which comprises a stainless steel tube or similar channel for guiding a dummy sourcewire 63 from "Y" connector 82 to dummy wire drive 90 (shown in FIG. 4). Mounted along dummy wire guide is dummy wire home sensor 52, which comprises an optical or mechanical switch adapted for detecting the presence or absence of dummy sourcewire 63 in dummy wire guide 78. In the embodiment of FIG. 1, the dummy wire home sensor 52 comprises a switch of generally similar construction and operation as overtravel switch 73. When dummy wire home sensor 52 detects the presence of the tip of dummy wire, this information is inputted into control system 100 to provide an accurate indication of the position of the dummy source of dummy sourcewire 63 as it is fed into the catheter attached to turret 80.

Referring now to FIG. 4, which comprises a view of the right interior side of an afterloader incorporating features of the present invention, dummy wire guide 78 continues generally downward to dummy drive mechanism 90, which comprises a similar drive mechanism as active drive mechanism 20, except that since the dummy drive system does not incorporate an emergency retract feature, the drive belt of dummy drive mechanism does not require a tension release mechanism. Accordingly, it is tensioned by a simple elastic member, such as a spring, rather than a solenoid system. The remainder of the elements of the dummy sourcewire drive/ storage system function in a manner similar to the corresponding elements of the active sourcewire drive/storage system with the dummy sourcewire transferred by transfer tube 54 to encoder wheel 112 of dummy wire storage feed mechanism 110 and into an open distal end 56 of dummy wire storage tube 58. As with the active drive system, a dummy overtravel sensor 120 detects an end of the dummy sourcewire to prevent a broken wire or other malfunction from disengaging the dummy sourcewire from the encoder and drive mechanism. Similarly, dummy park switch 122 detects the proximal end of the dummy sourcewire to confirm that is has been fully retracted.

Also shown in FIG. 4 is a representation of computer control system 100 and radiation monitoring circuitry 130. The function of computer control system 100 is generally similar to the function described in the foregoing '834 patent except for the addition of functional blocks to receive and respond to information from bar code scanner 81 and force feedback sensor 32 and other conventional changes that do not constitute a part of the present invention. Radiation monitoring circuitry 130 serves two important functions, internal and external radiation monitoring. Circuit 130 monitors internal radiation using a radiation monitoring device 132, comprising a conventional Geiger-Mueller tube, silicon diode or similar radiation monitoring device, which senses radiation as the active wire is advanced out of radiation safe 70 and confirms that the source is no longer shielded. Radiation monitoring circuitry 130 communicates this information to control system 100. Similarly, radiation monitoring device 132 senses that the radiation is present during the treatment, senses the increase in radiation as the source is retracted toward the safe 70 after treatment, and senses a rapid drop in radiation as the source is withdrawn into the safe. The information from radiation monitoring circuitry 130 is correlated to determine if the radiation behavior was within acceptable boundaries. If the radiation behavior is outside acceptable limits, indicating that the source has not properly retracted into the safe, or that the source is no longer present at the tip of the source wire (for example if the source has broken off inside the patient) control system 100 alerts the operator to the fault condition so that remedial measures can be taken.

Depending on the intensity of the radiation source used, it may be necessary to provide radiation shielding around the treatment area. Accordingly, in an embodiment of the present invention, a modular system of shielding would be provided. To ensure that the modular shielding is properly installed, a remote radiation monitoring device 134 is placed outside the treatment area. A fail safe circuit prevents the active sourcewire 62 from being advanced unless remote radiation monitoring device is properly connected and probed for proper function by radiation monitoring circuitry 130. If remote device 134 is functioning properly, sourcewire 62 is advanced briefly and a measurement taken by remote device 134. If the measurement is within acceptable limits, the modular radiation shielding has been properly installed and the treatment is allowed to commence. If, however, the measurement exceeds acceptable limits the sourcewire 62 is immediately withdrawn into radiation safe 70 and the operator alerted to the fault condition (e.g. by sounding audible alarm 140).

In use, after the non-radioactive dummy sourcewire has been advanced and the appropriate distance treatment intervals and other information programmed into the control system as discussed in the aforementioned '834 patent, the active sourcewire is advanced from the safe into the catheter at a rate of up to about 100 centimeters per second. As the sourcewire 62 advances, the control system interrogates the force sensor 32 at intervals of approximately 0.3 millimeters. The control system compares the force readings to a predetermined force profile which has been preprogrammed into the control system based on, among other things, the type of catheter and the treatment being performed. The control system makes adjustments to the speed at which the sourcewire 62 advances at the same 0.3 millimeter intervals to keep the speed of advancement at the highest possible rate while maintaining the force level within the predetermined force profile. Since the time between measurements and corrections is a function of distance, the rate of measurements/corrections is dynamic with respect to wire velocity. At a velocity of 100 centimeters per second, for example, a 0.3 millimeter measurement interval translates to a force reading and corresponding speed adjustment occurring about every 300 microseconds.

It should be understood, however, that the scope of the invention is not limited to measurement and/or adjustment intervals of 0.3 millimeters. The precise distance interval at which a measurement is taken and a correction made depends primarily on the material and thickness of the catheter being used. The interval chosen must be short enough to permit the afterloader to respond to the increased force caused by a sourcewire beginning to puncture a catheter quickly enough to stop advancement of the sourcewire before it has passed through the thickness of the catheter wall (including any stretching of the catheter). Accordingly, measurements must be taken at shorter distance intervals where thin walled and/or relatively non-deformable catheters are employed. Measurements can be taken at longer distance intervals where thick walled and/or highly deformable catheters are employed.

Although the preferred method is to take measurements at fixed distance intervals, a fixed time interval also may be used. Preferably, if a fixed time interval is used, it should be at least as short as the time interval of the fastest wire velocity for the particular catheter being employed, again to ensure that the afterloader can respond before the wire can puncture a catheter.

In addition to the preprogrammed force profiles, the control system responds to sudden changes and absolute force limits. In the event the force measurement rises abruptly or exceeds an absolute threshold, the advancement is immediately arrested but the force measurements continue at regular intervals. If the force measurements indicate a gradual reduction in the load on the sourcewire, the controller recognizes this as a tight curve and resumes advancement of the sourcewire. If, however, after a predetermined period the load on the sourcewire does not fall off, the controller recognizes this as an obstruction or impending catheter breach and initiates retraction of the sourcewire.

Figure 5:
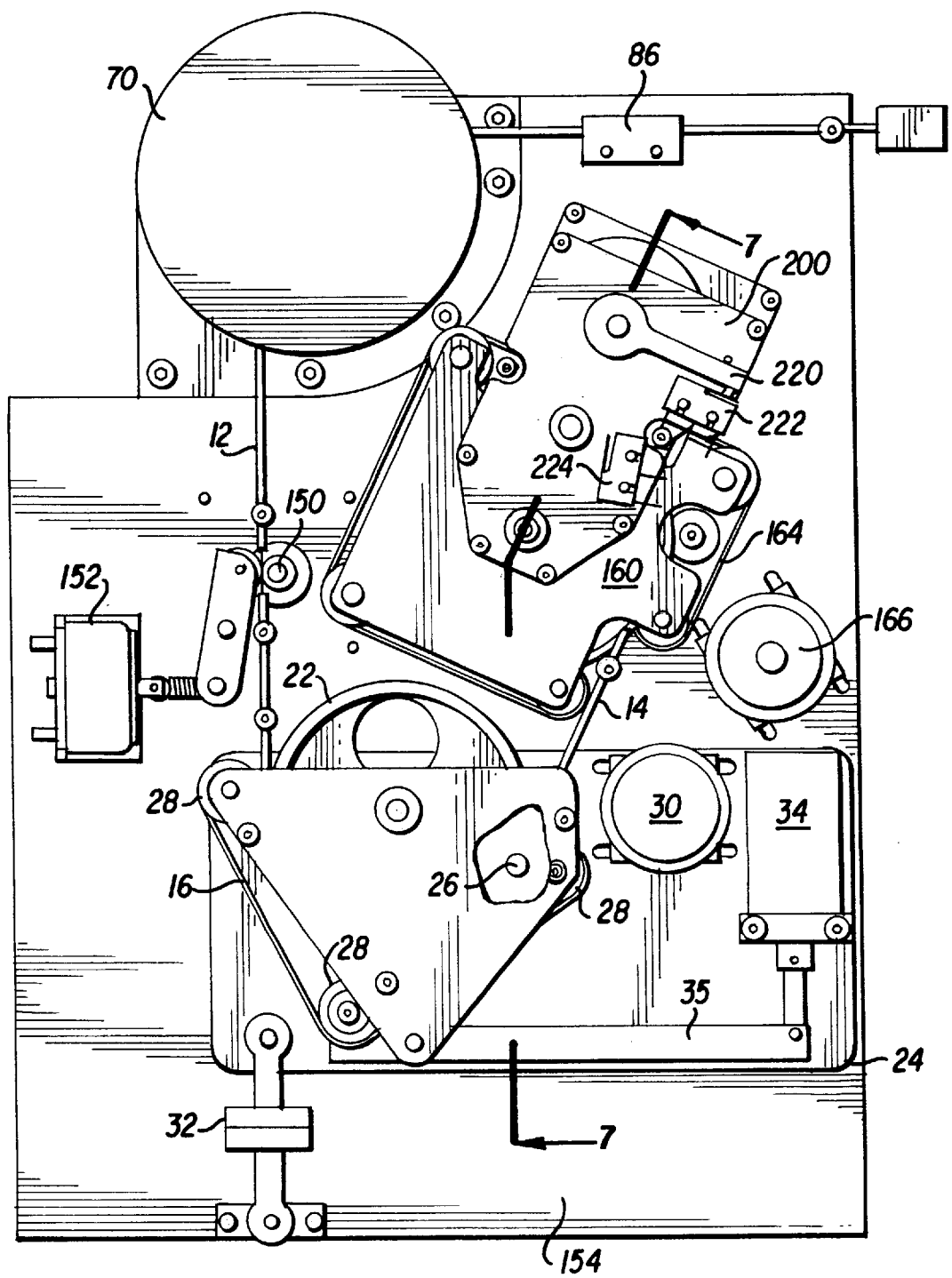
FIG. 5 is an enlarged left side view with a portion broken away to reveal a sourcewire storage and drive system according to an alternate embodiment of the present invention.

FIG. 5 is a plan view of an alternate embodiment of a wire drive/storage system according to the present invention, in which like elements have like numbers to the embodiment of FIGS. 1–4. The drive mechanism 20 includes carriage 24, drive wheel 22 driven by drive motor 30, and endless belt 16 tensioned by tension solenoid 34 about capstans 28 via tensioner arm 35. Carriage 24 is pivotally mounted by pivot 26, which is aligned with the axis of transfer tube 14. Carriage 24 is free to rotate about pivot 26 subject to the constraint of force sensor 32. In the present embodiment, drive motor 30 is actually a combination motor with encoder, thereby allowing the rotation of motor 30, and therefore indirectly the advancement of sourcewire 62, to be monitored. An optional redundant encoder 150 directly contacts the sourcewire 62 as it passes from the drive mechanism to the radiation safe 70. Sourcewire 62 is biased against the capstan of redundant encoder 150 by redundant encoder engagement solenoid 152.

Figure 6:
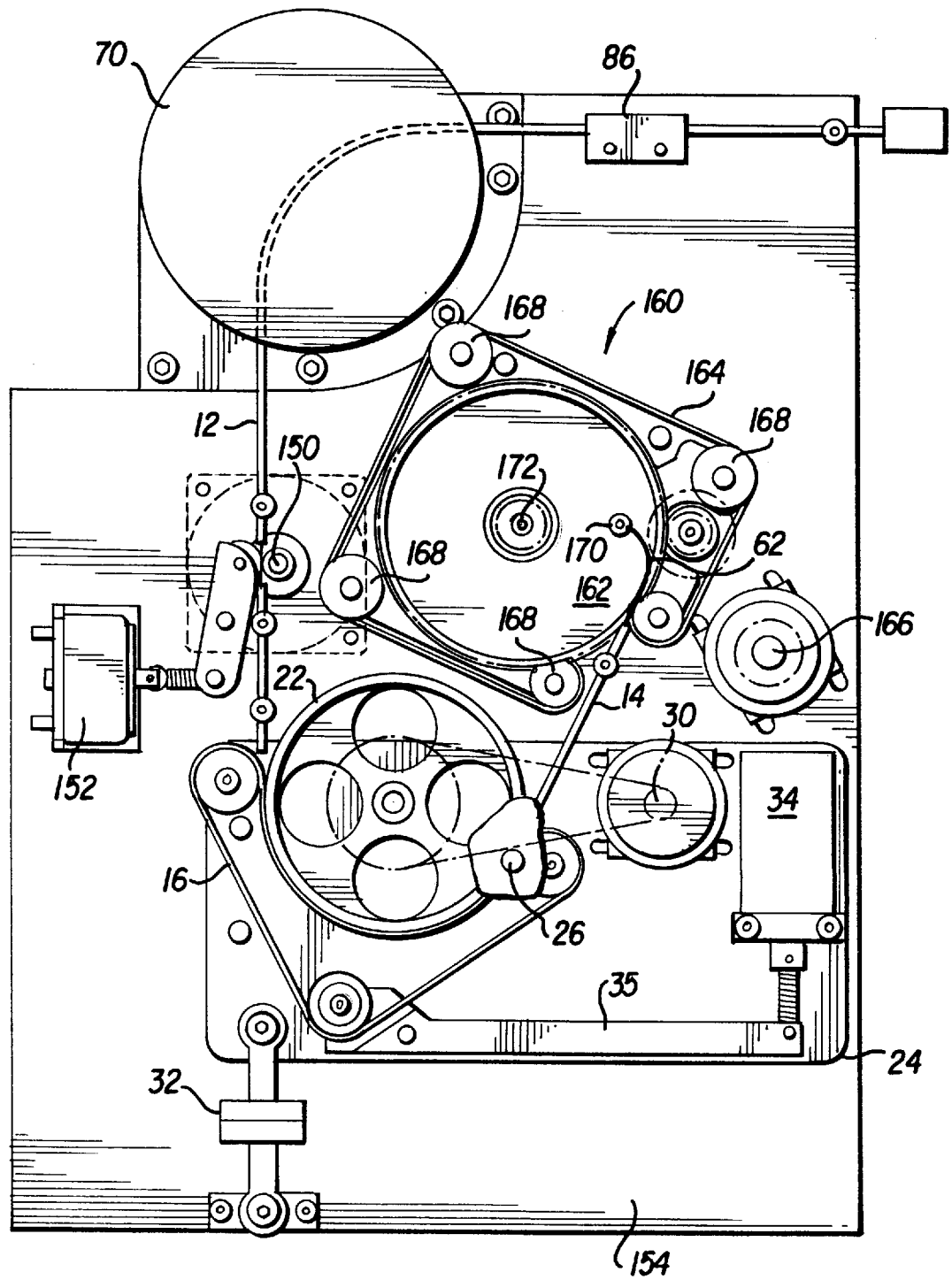
FIG. 6 is the enlarged left side view of FIG. 5 with additional portions broken away to reveal additional details of the sourcewire storage and drive system of FIG. 5.
Figure 7:
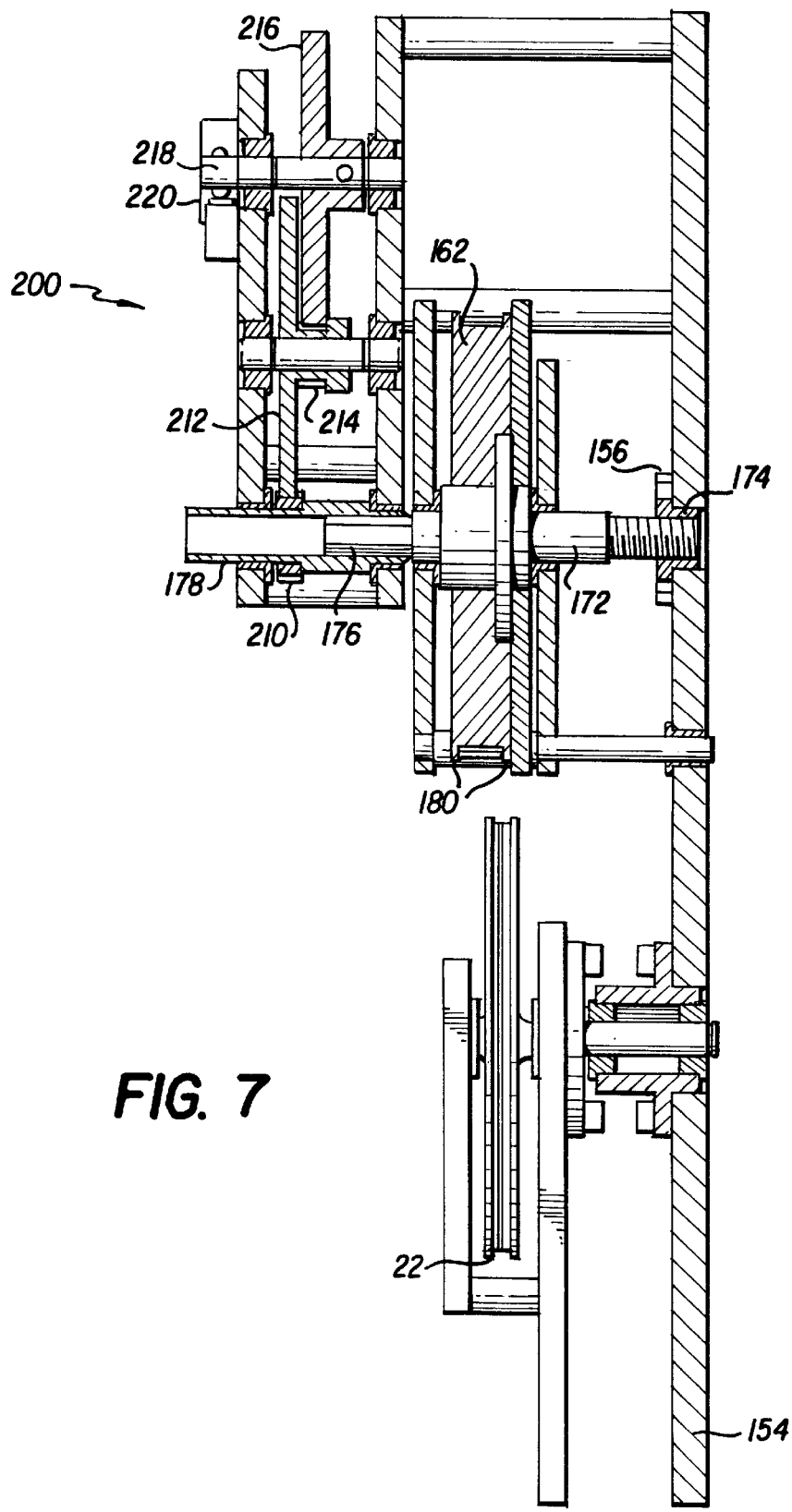
FIG. 7 is a partial cross sectional view of the sourcewire storage and drive system of FIG. 5 taken at line 7—7.

FIG. 6 is the plan view of FIG. 5 with additional portions broken away to reveal additional details. FIG. 7 is a partial cross-sectional view of the embodiment of FIG. 5 taken at line 7—7. Referring to FIG. 6, the wire storage means comprises a take up reel mechanism 160 which comprises a flanged cylindrical drum 162 having a flat or grooved outer circumferential surface and a fixed shaft 172 therethrough. The proximal end of sourcewire 62 is attached to a fixed attachment point 170 of drum 162. An endless belt 164 is disposed between a plurality of capstans 168 and the outer circumferential surface of drum 162 between the flanges 180 (FIG. 7) of drum 162. Storage drive motor 166, comprising a conventional stepper or servo motor drives drum 162 by conventional means in synchronous operation with drive wheel 22 as controlled by control system 100. Position feedback is provided by an encoder integral to or conventionally attached to drive motor 166.

Shaft 172 of drum 162 has a threaded end 174, which is threaded through a threaded bearing 156 fixed to a subframe 154. Preferably, the lead of threaded end 174 is approximately equal to the diameter of sourcewire 62 such that drum 162 is advanced toward or away from subframe 154 a distance equal to the diameter of sourcewire 62 for each revolution of drum 162. According to this arrangement, sourcewire 62 will lay flat against the surface of drum 162 without overlapping itself and, more importantly, so that the point of departure of sourcewire 62 from drum 162 relative to transfer tube 14 remains fixed regardless of the quantity of sourcewire stored on the drum.

Shaft 172 of drum 162 also has a splined end 176, which engages wire position limit mechanism 200. Limit mechanism 200 comprises a multiple pass, low backlash gear reduction mechanism comprising a first pinion 210 fixed to outer spline 178. Pinion 210 drives a first gear 212 which is fixed to a second pinion 214 which, in turn, drives a second gear 216 which is fixed to output shaft 218. Fixed at the end of output shaft 218 is arm 220, which rotates responsive to rotation of shaft 218 to contact at both ends of its travel limit switches 224 and 222 (FIG. 5), which comprise conventional mechanical or optical switches. By virtue of the multiple pass gear reduction, arm 220 rotates approximately ¾ revolution responsive to the full extension of sourcewire 62. Alternately, a micro chain, cogged belt or similar highly precise shaft reduction mechanism may be used to provide the appropriate reduction between shaft 172 and shaft 218.

Limit switch 224 is contacted when sourcewire 62 is fully retracted onto drum 162 and the radioactive tip of sourcewire 62 is within safe 70. Accordingly, limit switch 224 functions analogously to active park switch 64 of the embodiment of FIGS. 1–4. Similarly limit switch 222 is contacted if sourcewire 62 is overextended. Accordingly, limit switch 222 functions to some extent analogously to active overtravel switch 73 of the embodiments of FIGS. 1–4 to detect a condition when the controller is overadvancing the sourcewire. Optionally, an overtravel switch that senses the presence of the sourcewire in transfer tube 16 may be incorporated in addition to limit switch 222 as an added measure of safety in the event of a broken sourcewire.

Prior art afterloaders typically require source wires to be replaced by highly trained technicians, who manually load the replacement sourcewires into the afterloader and verify proper function of the systems that monitor the sourcewire location within the afterloader wire storage means. Where short half-life sources such as $^{32}P$ are used, the necessarily frequent replacement of sourcewire by trained technicians may present a significant cost. Accordingly, a readily replaceable sourcewire would be especially useful where short half-life sources such as $^{32}P$ are used.

As shown in FIGS. 8A and 8B, the compact storage system of FIGS. 5–7 may readily be configured as a readily replaceable modular drive "cassette." In the cassette afterloader configuration of FIG. 8A and 8B, the storage and drive systems are contained on a readily detachable subframe 154 which can be removed from the afterloader housing containing the control system and other systems. The cassette includes the sourcewire drive and storage systems, radiation safe, and also includes the sourcewire position monitoring devices which are, preferably, adjusted and verified by the manufacturer before the cassette is shipped to the user. Because the sourcewire is already loaded into the drive and the function of the sourcewire monitoring devices verified before the cassette is delivered to the user, it can be installed by a relatively unskilled employee.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. An apparatus for advancing a radioactive source into and out of a catheter implanted in the body of a patient comprising:

a housing adapted to receive an end of said catheter;

an elongate lead adapted to support the radioactive source at an end thereof;

means mounted to said housing for storing said elongate lead;

a drive mechanism mounted to said housing for advancing said elongate lead into said catheter;

a force sensor for detecting force required to advance said elongate lead into said catheter and for generating an output signal indicative of said force;

an encoder for determining displacement of said elongate lead and for generating an output signal indicative of said displacement; and an electronic control system comprising circuit means responsive to the signals from said force sensor and from said encoder for controlling advancement of said elongate lead into and out of said catheter.

2. The apparatus of claim 1 wherein said drive mechanism comprises a cylindrical disk having a single groove of one revolution disposed on an outer surface thereof, said disk being rotated about an axis thereof, said groove adapted for receiving said elongate lead from said storage means and advancing said elongate lead into said catheter, said elongate lead contacting said groove for at least about 10 degrees of arc.

3. The apparatus of claim 2 further including:
a guide tube for preventing buckling of said elongate lead, said guide tube having an open end fixed at a point proximal to a point where said elongate lead exits said groove tangent to said cylindrical disk as said elongate lead is advanced into said catheter.

4. The apparatus of claim 3 further including:
a second guide tube for preventing buckling of said elongate lead, said second guide tube having an open end fixed at a point proximal to a point where said elongate lead exits said groove tangent to said cylindrical disk as said elongate lead is retracted from said catheter and conveyed to said lead storage means.

5. The apparatus of claim 2 further including means for urging said elongate lead against said groove.

6. The apparatus of claim 5 wherein said urging means comprises an endless belt disposed between a plurality of capstans and said outer circumferential surface of said cylindrical disk.

7. The apparatus of claim 1 further including:
a plurality of capstans adjacent to said outer circumferential surface of said cylindrical disk for retaining said elongate lead in said groove.

8. The apparatus of claim 1 wherein said storage means comprises an elongate tube mounted to said housing and having an opening proximal to said drive mechanism.

9. The apparatus of claim 1 wherein said storage means comprises a substantially cylindrical drum having an outer cylindrical surface and being rotated about an axis thereof, said storage means further including means for displacing said drum along said axis responsive to rotation of said drum for urging said elongate lead to wind flat against said drum without overlapping.

10. The apparatus of claim 9 further including means for urging said elongate lead against said outer cylindrical surface of said drum.

11. The apparatus of claim 9 wherein said urging means comprises a plurality of capstans.

12. The apparatus of claim 9 wherein said urging means comprises an endless belt disposed between a plurality of capstans and said outer circumferential surface of said drum.

13. The apparatus of claim 1 wherein said drive mechanism and said storage means are housed in a separate unit that is readily detachable from said housing.

14. The apparatus of claim 1 wherein said drive mechanism is pivotally attached to said housing and said force sensor comprises a load cell mounted along the axis of said elongate lead exiting said drive mechanism as it is advanced toward said catheter.

15. The apparatus of claim 13 wherein said pivotal attachment is substantially along the axis of said elongate lead entering said drive mechanism as it is advanced out of said storage means.

16. The apparatus of claim 1 wherein said catheter is slidably attached to said housing and said force sensor comprises a load cell adapted to sense a force tending to displace said catheter.

17. The apparatus of claim 1 further including a direction changing capstan, said direction changing capstan slidably mounted to said housing and wherein said force sensor comprises a load cell adapted to sense a force tending to displace said direction changing capstan.

18. The apparatus of claim 1 further including a catheter receiver for storing a plurality of catheters, at least one of said catheters having catheter information associated therewith, a scanner for reading the catheter information, said electronic control system including further circuit means responsive to said catheter information for controlling advancement of said elongate lead into and out of said catheter.

19. The apparatus of claim 18 wherein said catheter information is affixed to said at least one catheter.

20. The apparatus of claim 18 wherein said scanner is incorporated into said catheter receiver.

21. The apparatus of claim 1 further including a radiation safe for storing said radioactive source when not in use and further including an internal radiation sensor for verifying location of said radiation source within or without said radiation safe.

22. The apparatus of claim 1 further including a shield external to said housing and an external radiation sensor for verifying the radioactive integrity of said shield.

23. The apparatus of claim 19 wherein said catheter information comprises a bar code affixed to at least some of said catheters.

24. The apparatus of claim 19 wherein said catheter information comprises a semiconductor chip embedded in at least some of said catheters.

25. The apparatus of claim 19 wherein said catheter includes a balloon affixed to said catheter, said catheter information including any of the type of catheter, the catheter length, the catheter balloon length, the location of the catheter balloon along the length of the catheter and an inventory control number.

26. The apparatus of claim 1 wherein said circuit means is responsive to said output signal of the force sensor to arrest advancement of said elongate lead when said output signal exceeds a predetermined value or rate of change.

27. The apparatus of claim 1 wherein said circuit means includes means for interrogating the output signal generated by the force sensor at predetermined intervals of displacement of said elongated lead or at predetermined time intervals.

28. The apparatus of claim 1 further including a catheter receiver for receiving said catheter, said catheter having catheter information associated therewith, a scanner for reading the catheter information, said electronic control system including further circuit means responsive to said catheter information for controlling advancement of said elongate lead into and out of said catheter.

29. The apparatus of claim 28, wherein said scanner is incorporated into said catheter receiver.

30. The apparatus of claim 1 wherein said force sensor includes means for monitoring a characteristic of said drive mechanism for advancing said elongate lead into said catheter.

31. The apparatus of claim 30 wherein said drive mechanism includes a drive motor, said monitoring means comprising a current measuring circuit for monitoring the current supplied to said drive motor.

32. An apparatus for advancing a radioactive source into and out of a catheter implanted in the body of a patient comprising a housing, an elongate lead adapted to support the radioactive source at an end thereof, a modular drive cassette replaceably mounted to said housing, said modular drive cassette having means for storing said elongate lead and drive means for advancing said elongate lead into said catheter and means for attaching and detaching said modular drive cassette to said housing for ready replacement of the cassette with another cassette having a new elongate lead with a radioactive source at the end thereof.

33. The apparatus of claim 32 including a force sensor for detecting the force required to advance said elongate lead into said catheter and for generating an output signal proportional to said force, an encoder for determining displacement of said elongate lead and for generating a signal indicative of said displacement and a control system comprising circuit means responsive to said signals for controlling advancement of said elongate lead into and out of said catheter in proportion to the output signal generated by said force sensor.

34. The apparatus of claim 33 wherein said circuit means is responsive to said output signal of the force sensor to arrest advancement of said elongate lead when said output signal exceeds a predetermined value or rate of change.

35. The apparatus of claim 33 wherein said circuit means includes means for interrogating the output signal generated by the force sensor at predetermined intervals of displacement of said elongated lead or at predetermined time intervals.

36. An apparatus for advancing and retracting a radioactive source into and out of the body of a patient comprising:

a frame;

an elongate lead adapted to support the radioactive source at an end thereof;

means mounted to said frame for storing said elongate lead;

drive means mounted to said frame for advancing said elongate lead along a path of travel into the patient;

a force sensor for detecting the force required to advance said elongate lead into the patient and for generating an output signal proportional to said force; and circuit means responsive to the output signal of said force sensor for controlling advancement of said elongate lead into the patient in proportion to the output signal generated by said force sensor.

37. The apparatus of claim 36 including an encoder for determining displacement of said elongate lead along the path of travel.

38. The apparatus of claim 36, including a housing for supporting said frame, said elongate lead being stored in a cassette, and means mounted to said housing for replaceably attaching said cassette to said housing.

39. An apparatus for advancing a radioactive source along a tortuous path to a target site in the body of a patient comprising:

a housing adapted to receive a proximal end of a catheter implanted in the patient along said tortuous path with a distal end of the catheter at or near the target site;

an elongate lead having a proximal end and a distal end, said radioactive source being secured at the distal end of the lead;

a radiation-proof safe coupled to said housing for storing at least the distal end of the lead when not advanced into the patient;

drive means mounted to said housing and secured to the proximal end of the lead for selectively advancing the distal end of the lead from the safe and into the catheter via the housing, and for selectively retracting the distal end of the lead into the safe;

a force sensor for detecting the magnitude of the force exerted by the drive means on the lead during advancement of the distal end thereof through the catheter and for generating an output signal indicative of said force; and feedback control means responsive to the magnitude of the exerted force detected by the force sensor for adjustment thereof to prevent buckling of the lead or puncture of the catheter when the distal end of the lead encounters obstructions or curves in the tortuous path during advancement thereof through the catheter.

40. An apparatus for advancing a radioactive source into and out of a catheter implanted in a patient, comprising an elongate lead having said radioactive source secured at the distal end thereof, drive means for advancing and retracting the distal end of said lead into and from the catheter, a modular cassette replaceably mounted to said drive means and including means for storing at least the distal end of the lead in a radiation-proof safe, and means for attaching and detaching the modular cassette to the drive means for ready replacement of the cassette with another cassette having a new elongate lead with radioactive source at the distal end thereof.

41. A method of advancing a radioactive source along a tortuous path to a target site in the body of a patient, comprising:

implanting a catheter in the patient along said tortuous path with a distal end of the catheter at or near the target site;

storing at least the distal end of an elongate lead having said radioactive source secured at the distal end thereof in a radiation-proof safe when not advanced into the patient;

selectively advancing the distal end of the lead from the safe and into the catheter;

detecting the magnitude of the force exerted on the lead during advancement of the distal end thereof through the catheter;

responding to feedback of the magnitude of the detected exerted force to adjust the exerted force to prevent buckling of the lead or puncture of the catheter when the distal end of the lead encounters obstructions or curves in the tortuous path during advancement thereof through the catheter; and selectively retracting the distal end of the lead into the safe after completing a procedure therewith.

* * * * *